(12) United States Patent
Zikria (10) Patent No.: US 12,051,492 B2
(45) Date of Patent: Jul. 30, 2024

(54) SYSTEMS AND METHODS TO DETERMINE A THERAPY REGIMEN TO TREAT ASTHMA OF A SUBJECT

(71) Applicant: AsthmaTek, Inc., Danville, CA (US)

(72) Inventor: Jemal Dean Zikria, Danville, CA (US)

(73) Assignee: AsthmaTek, Inc., Danville, CA (US)

( * ) Notice: Subject to any disclaimer, the term of this patent is extended or adjusted under 35 U.S.C. 154(b) by 525 days.

(21) Appl. No.: 17/162,413

(22) Filed: Jan. 29, 2021

(65) Prior Publication Data

US 2022/0246260 A1    Aug. 4, 2022

(51) Int. Cl.
  *G16H 20/10* (2018.01)
  *G06N 20/00* (2019.01)
  *G16H 10/60* (2018.01)
  *G16H 40/67* (2018.01)

(52) U.S. Cl.
  CPC ............ *G16H 20/10* (2018.01); *G06N 20/00* (2019.01); *G16H 10/60* (2018.01); *G16H 40/67* (2018.01)

(58) Field of Classification Search
  CPC ........ G16H 20/10; G16H 10/60; G16H 40/67; G16H 20/30; G16H 20/13; G16H 50/20; G06N 20/00
  See application file for complete search history.

(56) References Cited

U.S. PATENT DOCUMENTS

| | | | |
|---|---|---|---|
| 6,958,691 B1 | 10/2005 | Anderson | |
| 8,491,493 B2 | 7/2013 | Colquitt | |
| 11,123,505 B2 | 9/2021 | Oddo | |
| 11,450,416 B2 | 9/2022 | Pillarisetty | |
| 2005/0172958 A1 | 8/2005 | Singer | |
| 2008/0261322 A1 | 10/2008 | Burdinski | |
| 2010/0196483 A1 | 8/2010 | Muellinger | |
| 2013/0053719 A1 | 2/2013 | Wekell | |
| 2013/0181832 A1* | 7/2013 | Landau | G08B 21/02 340/539.12 |

(Continued)

OTHER PUBLICATIONS

PCT International Search Report and Written Opinion, PCT Application No. PCT/US2022/011683, mailed Mar. 24, 2022.

(Continued)

*Primary Examiner* — Charles R Kasenge
(74) *Attorney, Agent, or Firm* — Esplin & Associates, PC (57) ABSTRACT

Systems and methods to determine a therapy regimen to treat asthma of a subject are disclosed. Exemplary implementations may: store a condition impact assessment and multiple therapy regimens for treating asthma; obtain subject information for the subject, wherein the subject information includes (i) environmental conditions at or around a physical location of the subject, (ii) results of remote diagnostic tests for the subject, and (iii) physician-certified condition information including results to physician-administered diagnostic tests for the subject; obtain the multiple therapy regimens; obtain the condition impact assessment; determine a particular therapy regimen from the multiple therapy regimens as an effective therapy regimen for a period of time based on the subject information and condition impact assessment; and define the effective therapy regimen as a current therapy regimen; and transmit the current therapy regimen to a subject client computing platform associated with the subject for presentation to the subject.

16 Claims, 3 Drawing Sheets

(56) References Cited

U.S. PATENT DOCUMENTS

| | | |
|---|---|---|
| 2014/0278552 A1 | 9/2014 | Hold |
| 2015/0081334 A1 | 3/2015 | Dulin |
| 2015/0126888 A1 | 5/2015 | Patel |
| 2015/0199490 A1 | 7/2015 | Iancu |
| 2015/0250408 A1 | 9/2015 | Ssenyange |
| 2016/0228037 A1 | 8/2016 | Bubis |
| 2016/0293054 A1 | 10/2016 | Milton-Edwards |
| 2017/0000382 A1 | 1/2017 | Leydon |
| 2017/0212739 A1 | 7/2017 | Catiller |
| 2017/0215790 A1 | 8/2017 | Levinson |
| 2018/0060494 A1* | 3/2018 | Dias ................ G16H 70/20 |
| 2018/0225419 A9 | 8/2018 | Anthony |
| 2018/0356429 A1 | 12/2018 | Morimoto |
| 2019/0350466 A1 | 11/2019 | Boschetti Sacco |
| 2020/0135334 A1 | 4/2020 | Rajasekhar |
| 2020/0253547 A1 | 8/2020 | Harris |
| 2020/0390400 A1 | 12/2020 | Ssenyange |
| 2021/0106776 A1 | 4/2021 | Milton-Edwards |
| 2022/0218290 A1 | 7/2022 | Zikria |
| 2022/0233093 A1 | 7/2022 | Zikria |

OTHER PUBLICATIONS

PCT International Search Report and Written Opinion, PCT Application No. PCT/US2022/011698, mailed Apr. 8, 2022.
PCT International Search Report and Written Opinion, PCT Application No. PCT/US2022/011457, mailed Apr. 6, 2022.

* cited by examiner

SYSTEMS AND METHODS TO DETERMINE A THERAPY REGIMEN TO TREAT ASTHMA OF A SUBJECT

FIELD OF THE DISCLOSURE

The present disclosure relates to systems and methods to determine a therapy regimen to treat asthma of a subject.

BACKGROUND

Individuals with asthma may only monitor and treat for his/her asthma symptoms, conditions, and causes. However, the individuals often do not monitor their conditions and causes correctly nor treat their symptoms correctly without guidance.

SUMMARY

One aspect of the present disclosure relates to a system configured to determine a therapy regimen to treat asthma of a subject. Electronic storage may store multiple therapy regimens, condition impact assessments, and/or other information. The subject may follow one of the multiple therapy regimens determined by the system. The condition impact assessments may indicate how much the asthma is impeding on the subject and their breathing functionality at a time of such assessment. Subject information informative of the asthma of the subject and a condition impact assessment may be obtained to facilitate determination of an effective therapy regimen that the subject follows or attempts to follow. The effective therapy regimen may be defined as the current therapy regimen, which may include changing/updating to the current therapy regimen from a previous one. The current therapy regimen may be transmitted to a subject client computing platform for presentation to the subject. Therefore, the subject may follow a therapy regimen that is more appropriate given the subject information, the condition impact assessment, and/or other information related to their asthma. Determination of the current therapy regimen by the system may alleviate a physician from determining when, how, and why the current therapy regimen should be adjusted for the subject.

One aspect of the present disclosure relates to a system configured to determine a therapy regimen to treat asthma of a subject. The system may include one or more hardware processors configured by machine-readable instructions, electronic storage, and/or other components. Instruction components may include one or more of information obtainment component, therapy regimen component, and/or other instruction components.

The electronic storage may be configured to store a condition impact assessment and multiple therapy regimens for treating asthma. The condition impact assessment may indicate a present impact of asthma on the subject. Individual therapy regimens may correspond to a particular impact of asthma on the subject and/or a particular condition of asthma.

The information obtainment component may be configured to obtain subject information for the subject. The subject information may include (i) environmental conditions at or around a physical location of the subject, (ii) results of remote diagnostic tests for the subject, and (iii) physician-certified condition information including results to physician-administered diagnostic tests for the subject.

The therapy regimen component may be configured to obtain the multiple therapy regimens from the electronic storage. The therapy regimen component may further be configured to obtain the condition impact assessment from the electronic storage. The therapy regimen component may be configured to determine a particular therapy regimen from the multiple therapy regimens as an effective therapy regimen for a period of time based on the subject information and the condition impact assessment.

The therapy regimen component may be configured to define the effective therapy regimen as a current therapy regimen. The therapy regimen component may be configured to transmit the current therapy regimen to a subject client computing platform associated with the subject for presentation to the subject.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
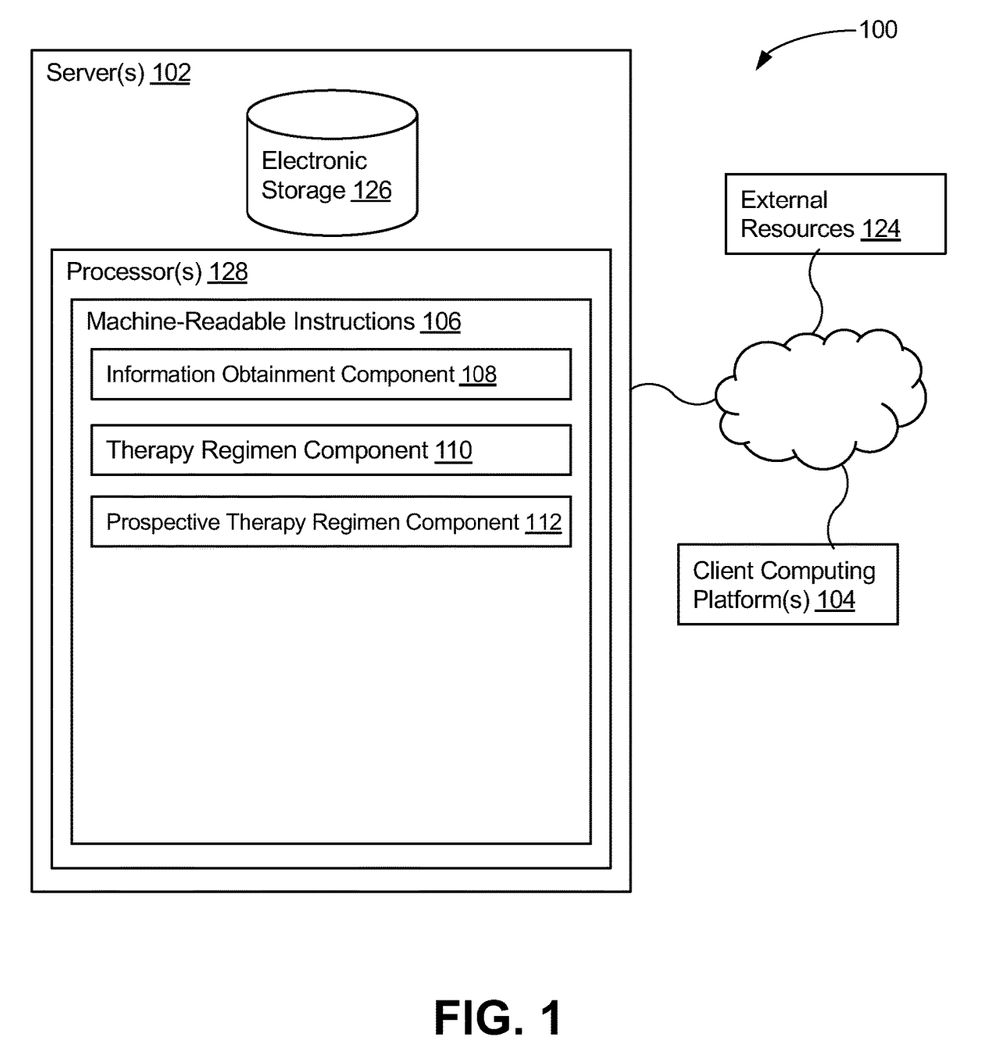
FIG. 1 illustrates a system configured to determine a therapy regimen to treat asthma of a subject, in accordance with one or more implementations.

FIG. 1 illustrates a system 100 configured to determine a therapy regimen to treat asthma of a subject, in accordance with one or more implementations. In some implementations, system 100 may include one or more servers 102, client computing platforms 104, electronic storage 126, and/or other components. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-topeer architecture and/or other architectures. Subjects may access system 100 via client computing platform(s) 104.

Server(s) 102 may be configured by machine-readable instructions 106. Machine-readable instructions 106 may include one or more instruction components. The instruction components may include computer program components. The instruction components may include one or more of information obtainment component 108, therapy regimen component 110, prospective therapy regimen component 112, and/or other instruction components.

Electronic storage 126 may be configured to store one or more condition impact assessment, multiple therapy regimens for treating asthma, and/or other information. A condition impact assessment may indicate a present impact of asthma on the subject and their breathing functionality at the time conducted. The present impact may be positive or negative. A positive present impact may indicate that the breathing functionality of the subject is not impeded by or less impeded by the asthma. For example, the positive present impact may be related to an improvement to the asthma of the subject and/or compliance with a specified and/or current therapy regimen. A negative present impact may indicate that the breathing functionality of the subject is impeded by the asthma. For example, the negative present impact may be related to a lack of compliance with the specified therapy regimen and/or the subject in physical locations or contextual environments that trigger asthma symptoms. Electronic storage 126 may be configured to store past condition impact assessments and a current condition impact assessment of the subject that are associated with a time at which they were conducted.

In some implementations, the present impact may be determined based on changes in subject information as described in co-pending U.S. application Ser. No. 17/156,277 entitled "SYSTEMS AND METHODS TO PROVIDE A PHYSICIAN INTERFACE THAT ENABLES A PHYSICIAN TO ASSESS ASTHMA OF A SUBJECT AND PROVIDE THERAPEUTIC FEEDBACK", the disclosure of which is incorporated by reference in its entirety herein. The changes in the subject information may indicate asthma symptoms for the subject, or a lack of asthma symptoms and good breathing functionality. Asthma symptoms may include shortness of breath, wheezing, coughing, chest pain, tightness of chest, rapid breathing, and/or other asthma symptoms.

By way of non-limiting example, changes in the subject information (further defined herein) that indicate the subject has one or more of the asthma symptoms may include increases in one or more of environmental conditions (e.g., the pollen levels, the elevation, the mold, the dust and dander, etc.), elevated values of subject health information (e.g., elevated heart rate), low values of subject health information, elevated results to remote diagnostic tests (e.g., a remote fractional exhaled nitric oxide (FeNO) test), low results to remote diagnostic tests (e.g., a remote spirometry test), elevated results to physician-administered diagnostic tests, low results to physician-administered diagnostic tests, and/or other changes in the subject information.

To indicate the subject has a negative present impact from the asthma symptoms, one or more of the changes in the subject information may occur, a particular amount of the changes in the subject information may occur, one or more of the changes in the subject information may reach respective specific threshold values, one or more of the changes in the subject information may reach respective specific threshold values within a particular amount of time, and/or other various combinations of the changes and/or other changes in the subject information. In some implementations, the threshold values may be of a metric unit, or lack thereof, of the respective subject information. The threshold values may be known values that indicate the subject has asthma symptoms or may be defined by the physician, the subject, system 100, and/or other individuals. The particular amount of time may be defined by the physician, the subject, system 100, and/or other individuals. A particular amount of the subject information changing may be defined by the physician, the subject, system 100, and/or other individuals. As such, in some implementations, the condition impact assessment may define a source for the present impact of the asthma on the subject. The source may be the changes in the subject information.

Individual therapy regimens may correspond to a particular impact of asthma on the subject and/or a particular condition of asthma (indicated by the subject information). In some implementations, the multiple therapy regimens may be specified by the physician and modified by the physician. The individual therapy regimens may be related to managing and/or improving the impact of asthma on the subject. The therapy regimens may be followed by or attempted to be followed by the subject to manage and/or improve the impact of asthma on the subject and their breathing functionality. By way of non-limiting example, the therapy regimens may include: inhaled corticosteroid (ICS) therapy, short acting beta agonists (SABA), long-acting beta agonists (LABA), zileuton (e.g., Zyflo), leukotriene receptor antagonists (LTRA), theophylline, omalizumab, other biologics for asthma, other asthma drug therapy, and/or other therapy.

By way of non-limiting example, the SABAs may include Asthavent® metered dose inhaler (MDI)/DP-Haler®/Revolizer® (Salbutamol), Berotec® MDI (Fenoterol), Venteze® MDI (Salbutamol), Ventolin® MDI/Accuhaler® (Salbutamol), and/or other SABAs. By way of non-limiting example, the LABAs may include Foratec DP-Haler®/Revolizer® (Formoterol), Oxis Turbuhaler® (Formoterol), Serevent® MDI/Accuhaler® (Salmeterol), and/or other LABAs. By way of non-limiting example, the other drug asthma therapies may include anticholinergics (i.e., a reliever), drug therapy combinations, preventers such as inhaled corticosteroids (ICS) and the leukotriene receptor antagonists, and/or other drug therapies. The anticholinergics may include Atrovent® MDI (Ipratropium Bromide), Ipvent-40® MDI (Ipratropium Bromide), Spiriva Handihaler® (Tiotropium), and/or other anticholinergics. The drug therapy combinations may include DP-Haler®/Revolizer@ (Budesonide+Formoterol), Seretide® MDI/Accuhaler® (Fluticasone+Salmeterol), Symbicord Turbuhaler® (Budesonide+Formoterol), and/or other drug therapy combinations. The inhaled corticosteroids may include Alvesco® MDI (Circlesonide), Beclate HFA® MDI (Beclomethasone), Budeflam DP-Haler®/Revolizer® (Budesonide), Budeflam HFA Gentle-Haler® (Budesonide), Flixotide® MDI/Accuhaler® (Fluticasone), Inflammide® MDI/Novolizer® (Budesonide), Pulmicort Turbuhaler® (Budesonide), QVAR® MDI (Beclomethasone), and/or other inhaled corticosteroids. The leukotriene receptor antagonists (LTRA) may include Singulair® tablets (Montelukast), and/or leukotriene receptor antagonists.

It is appreciated that the therapy regimens listed are not intended to be limiting and are for illustrative purposes only as there may be various other therapies (e.g., non-medicinal exercises) specified and/or therapy aids provided as the therapy regimens for the subject to treat their asthma, facilitate treating their asthma, and/or monitor therapy utility. For example, the other therapies may include particular exercises; adherence counseling for the subject (e.g., by the physician or other healthcare provider); avoidance of particular environmental conditions, contextual environments, physical locations, foods, and/or other triggers of asthma symptoms; and/or other therapies. In some implementations, the therapy regimens may include therapy aids such as educational material related to individual therapies (e.g., adherence online courses, drug therapy educational material), devices that facilitate adherence (e.g., Bluetooth Low Energy (BTLE) inhaler caps, electronic pill bottle caps, etc.), and/or other therapy aids.

In some implementations, the multiple therapy regimens may be constructed in a stepwise approach. The individual therapy regimens may incrementally step up to increase dosages and/or change drug therapies, other therapies, and/or therapy aids, and conversely may incrementally step down when appropriate determined (i.e., by therapy regimen component 110). For example, the stepwise approach to the multiple therapy regimens may step up beginning with the SABAs as needed; to a low-dose ICS; to a low-dose ICS with either one of a LABA, a LTRA, or Theophylline, or alternatively a medium lose ICS; to a medium-dose LABA; to a high-dose ICS with a LABA; to a high-dose ICS with a LABA and oral systemic Corticosteroids, and step down as appropriately determined by therapy regimen component 110.

Information obtainment component 108 may be configured to obtain the subject information for the subject. The subject information may include (i) the environmental conditions at or around a physical location of the subject, (ii) subject condition information (e.g., results of the remote diagnostic tests for the subject), (iii) physician-certified condition information, and/or other subject information. As used herein, the term "physician" may refer to a doctor, a clinician, a nurse, a nurse practitioner, an asthma educator, a respiratory specialist, and/or or other authorized medical practitioner or healthcare providers. In some implementations, the subject information may be stored in electronic storage 126 and obtained from such or obtained from other sources.

The environmental conditions at or around the physical location may be indicated by location information related to the physical location of the subject over time and/or future location information. The physical location may refer to where the subject is over time. The subject may be at, around, or near the physical location and other various physical locations for an amount time. The location information may indicate the physical location of the subject. The physical location of the subject may be of a contextual environment of the subject. The contextual environment may be the immediate space surrounding the subject and of which the subject is working or otherwise breathing in. For example, the contextual environment may be outdoors or indoors. The environmental conditions may be based on the location information.

The location information may include geographical position system (GPS) coordinates, an internet protocol (IP) address, a geolocation based on a subject client computing platform 104 associated with the subject and proximate cell towers, Wi-Fi location, and/or other information based on the subject client computing platform 104 that indicates their physical location. In some implementations, the location information may be obtained in an ongoing manner to ensure accuracy of the physical location indicated. In some implementations, subject movements may be tracked using a geography-based transmitter on client computing device 104 associated with the subject.

The term "ongoing manner" as used herein may refer to continuing to perform an action (e.g., obtain) periodically (e.g., every 30 seconds, every minute, every hour, etc.) until receipt of an indication to terminate. The indication to terminate may include powering off subject client computing platform 104, charging one or more of a battery of subject client computing platform 104, subject input (e.g., via a virtual button), and/or other indications of termination. For example, the subject may move 7 miles from an initial physical location indicated by the location information and the location information should be obtained again to indicate a more accurate physical location of the subject.

In some implementations, the location information may include location input obtained from the subject client computing platform 104 that is manually entered by the subject to indicate their physical location. For example, the location input may include GPS coordinates, a street address, a zip code, a city, the contextual environment (e.g., indoors or outdoors) and/or other location information. In some implementations, the amount of time, a start time, and/or an end time that the subject is at, around, or near the physical location may be manually input by the subject. For example, the subject may input a start time of 5 PM for 3 hours, or 5 PM-8 PM.

The future location information may indicate one or more future physical locations of the subject at a future time for a future period of time and/or future contextual environments of the subject. In some implementations, the future location information may be obtained from, derived from, or based on a calendar, to-do lists, and/or other information that information obtainment component 108 has access to. In some implementations, the future location information may include subject input obtained from the subject client computing platform 104 that is manually entered by the subject. The subject input may include GPS coordinates, a street address, a zip code, a city, the future contextual environment (e.g., indoors or outdoors) and/or other future location information. The future period of time, the future time, and/or a future end time that the subject is at, around, or near the future physical locations may be included in the subject input.

By way of non-limiting example, the environmental conditions may include values to one or more of pollen levels, weather, an elevation, mold, dust and dander, an air quality index, and/or other environmental conditions. In some implementations, the values may be numerical and associated with units of measure. In some implementations, the values may be non-numerical and generally characterize the respective environmental condition (e.g., good, okay, low, medium, moderate, fair, high, poor, extreme). The values of pollen levels may indicate how much of tree pollen, grass pollen, weed pollen, flower pollen, and/or other pollen is present in air. The values to the weather may include an outdoor temperature, precipitation, humidity, and/or other values indicative of the weather at or around the physical location. The values to the mold may indicate an amount of mold spores in a cubic meter of the air, or other measurement, at or around the physical location. The values of the dust and dander may indicate how much dust and dander from animal fur, hair, feathers, and/or other sources are in an indoor area and/or outdoor area. In some implementations, the values of the dust and dander may be based on the values to the weather and/or other environmental conditions that may exacerbate the dust and dander or may not. The values to the air quality index may indicate how polluted the air at the physical location is. In some implementations, the air may be polluted with the pollen, the dust and dander, the mold spores, and/or other pollutants.

In some implementations, information obtainment component 108 may be configured to obtain the location information and/or the future location information and determine the environmental conditions based on such. In some implementations, the environmental conditions that are based on the location information or the future location information may be obtained (e.g., from weather systems) by information obtainment component 108. Therefore, the environmental conditions for current physical locations and the future physical locations may be obtained or determined by information obtainment component 108.

In some implementations, the contextual environment may be the indoors (e.g., living room, office). In some implementations, the value to the air quality index may be based on air quality information from one or more digital air purification systems proximate to the subject in the indoor area. The one or more digital air purification systems may be proximate to the subject in the contextual environment, i.e., the indoor area, of the subject. The air quality information may convey ambient air quality measured in the contextual environment of the subject. The digital air purification systems may measure, calculate, derive from, or otherwise determine values indicative of quantities of dust and dander, mold, pollen level, and/or other information in the indoors.

In some implementations, the contextual environment may be the outdoors (i.e., the subject is outdoors). In some implementations, the value to the air quality index may be based on air quality information obtained from the external resources 124 for the outdoors. External resources 124 may include satellite systems that collect information about particles in the air, the dust and dander, the mold, the pollen level, and/or other external resources 124 that collect and/or provide air quality information for the outdoors.

In some implementations, the air quality information (obtained from the digital air purification system or external resources 124) may be associated with a particular time or period of time. In some implementations, the air quality information may be obtained in an ongoing manner. In some implementations, the air quality information may be obtained at a reoccurring predefined time and may convey the ambient air quality of past times or periods of time.

Thus, in some implementations, the values to the air quality index may be determined or otherwise derived from the air quality information obtained. In some implementations, information obtainment component 108 may be configured to obtain the values to the air quality index directly from and determined by external resources 124, the digital air purification systems, and/or other sources.

The subject condition information may define remote diagnostic information, subject health information, and/or other information. The subject condition information may include information related to asthma and general health of the subject. The remote diagnostic information may include past and most current results to remote diagnostic tests and medication administrators that the subject may conduct themselves at home, for example, as opposed to a clinic, doctors office, or other medical office. The remote diagnostic tests and medication administrators may include a remote FeNO test, a remote spirometry test, a remote peak flow test, a digital inhaler, and/or other remote diagnostic tests and medication administrators. The results may be associated with a date and/or time at which a given test or medication administration occurred. The subject condition information may be stored in electronic storage 126 and information obtainment component 108 may obtained the subject condition information. In some implementations, the subject condition information may be obtained by information obtainment component 108 from cloud storage or other storage.

A result to the remote FeNO test may determine an amount of lung inflammation of the subject. A result to the remote spirometry test may indicate how much air lungs of the subject is able to breathe in and out and how easily and fast the lungs are able to exhale the air. A result of the remote peak flow test may determine how fast the lungs are able to forcefully exhale after a full inhalation of air. The digital inhaler may indicate correctness of inhalation techniques of medication administered by the digital inhaler, frequency of the administrations, and/or other information related to medication administrations/consumptions via the digital inhaler. For example, the frequency of the administrations may indicate whether the patient is using the digital inhaler enough or too often. For example, the correctness of inhalation techniques may indicate whether the subject is positioning the digital inhaler at a correct angle during administration, shaking the digital inhaler enough or too much prior to use, and/or other correctness of inhalation techniques.

The subject health information may include values for one or more of cardiovascular parameters, sleep parameters, activity parameters, diet parameters, and/or other parameters. The subject health information (i.e., parameter included thereof) may specify measurable, recordable, and/or determined information. The values corresponding to the parameters included in the subject health information may be a particular value, numerical or non-numerical, that characterizes the subject.

By way of non-limiting example, the cardiovascular parameters may include a heart rate, a resting heart rate of the subject, a respiratory rate of the subject, blood pressure of the subject, oxygen saturation of the subject, heart variability, heartbeat strength, heartbeat rhythm, and/or other cardiovascular parameters. By way of non-limiting example, the sleep parameters may include hours of sleep, sleep quality, motion during sleep, breathing patterns during sleep, and/or other sleep parameters. By way of non-limiting example, the activity parameters may include minutes exercised; distance walked, ran, cycled, and/or swam; speed of the walk, the run, the cycle, and the swim; inclination of the walk, the run, and the cycled; acceleration, time standing, and/or other activity parameters. By way of non-limiting example, diet parameters may include caloric intake, weight, weight goal, height, body mass index (BMI), various vitamin intake, food restrictions, food intake, liquid intake, substance intake, and/or other diet parameters. Some of the subject health information may be obtained from one or more wearable devices worn by the subject. For example, the wearable devices may include an orientation sensor, a location sensor, a pressure sensor, a temperature sensor, a light sensor, an audio sensor, cardiovascular sensors, and/or other sensors. For example, the cardiovascular sensors may include an electrodermal activity (EDA), an electrocardiography (EKG or ECG) sensor, a blood volume pulse (BVP) sensor, a respiration sensor, a blood pressure sensor, and/or other cardiovascular sensors. Some or all of the subject health information may be measured, recorded, or otherwise determined at a medical office, remotely by the subject (e.g., at home), a pharmacy, and/or other location. It is to be expressly understood, however, that the subject health information obtained and the sensors that facilitation the obtainment are for the purpose of illustration and description only and are not intended as a definition of the limits of this disclosure.

In some implementations, information obtainment component 108 may be configured to receive manual subject condition information (i.e., remote diagnostic information, subject health information) the from client computing platform 104 associated with the subject described in FIG. 1. The manual subject condition information may be the same as the subject condition information though manually input by the subject via a graphical user interface presented on their subject client computing platform 104.

The physician-certified condition information may include results to physician-administered diagnostic tests for the subject. The physician-certified condition information may include physician-supervised diagnostic information, and/or other information collected by the physician related to the subject.

The physician-supervised diagnostic information may include past and most current results to the physician-administered diagnostic tests that include a physician-administered FeNO test, a physician-administered spirometry test, a physician-administered peak flow test, and/or other physician-administered diagnostic tests. The physician-administered FeNO test, the physician-administered spirometry test, and the physician-administered peak flow test, may be the same as or similar to the remote FeNO test, the remote spirometry test, and the remote peak flow test, respectively, though administered/conducted by the physician. In some implementations, the tests that are physician-administered may be conducted at a medical office, for example, or other setting (e.g., home of subject during house call). In some implementations, the physician-certified condition information may be obtained from clinical systems (e.g., associated with the medical office, hospitals, etc.), laboratory systems, outpatient clinic information technology (IT) systems, and/or other medical information systems, electronic storage 126, and/or external resources 124. Some or all of the physician-administered diagnostic tests may be conducted at a medical office, a pharmacy, or other location by the physician.

Information obtainment component 108 may be configured to obtain the multiple therapy regimens and/or other information from electronic storage 126. Information obtainment component 108 may be configured to obtain the condition impact assessments (i.e., past and/or current) and/or other information from electronic storage 126. One of the multiple therapy regimens may be a current therapy regimen that the subject follows or attempts to follow to improve or maintain their asthma symptoms. The current therapy regimen may change as the subject information, the condition impact assessment, and/or other information regarding the subject changes.

Therapy regimen component 110 may be configured to determine a particular therapy regimen from the multiple therapy regimens as an effective therapy regimen for a period of time based on the subject information, changes thereof, the condition impact assessments, the current therapy regimen, and/or other information. The effective therapy regimen may be a therapy regimen that is suitable/most appropriate given the subject information, the condition impact assessment, and/or other information characterizing the asthma and its impact on the subject. For example, the subject information may indicate a high result to a remote FeNO test for the subject and a negative impact of the asthma on the subject. The particular therapy regimen determined based on the high result and the negative impact may treat the asthma symptoms more intensely. The period of time may be a day, a set of days, a week, an amount of weeks, or other period of time that the subject is to follow the effective therapy regimen. The determination of the effective therapy regimen by determining the particular therapy regimen from the multiple therapy regimens may be reoccurring (e.g., once every week, every 3 days, etc.) as defined or modified by the physician and/or the subject, or as defined by system 100. In some implementations, the determination may occur responsive to receipt of a physician indication or subject indication (e.g., selecting a virtual button included on interfaces presented on their respective client computing platforms 104).

In some implementations, therapy regimen component 110 may be configured to receive a selected therapy regimen of the multiple therapy regimens from the subject client computing platform 104. Determining the effective therapy regimen may be further based on the selected therapy regimen. That is, the subject may select their own effective therapy regimen to follow or attempt to follow. In some implementations, the particular therapy regimen determined by therapy regimen component 110 may be different that the selected therapy regimen. Thus, determining the effective therapy regimen based on the particular therapy regimen (that is based on the subject information, the condition impact assessment, and/or other information) and the selected therapy regimen may include determining a combination of the selected therapy regimen and the particular therapy regimen. The combination may be a midpoint between the selected therapy regimen and the particular therapy regimen. The combination may include one or more therapies from each of the selected therapy regimen and the particular therapy regimen. In some implementations, the selected therapy regimen may be received to be the effective therapy regimen.

In some implementations, therapy regimen component 110 may be configured to transmit the effective therapy regimen to the physician client computing platform 104 for presentation to the physician. In some implementations, the presentation of the effective therapy regimen may be presented as a suggestion that the physician may accept, deny, or modify. Thus, in some implementations, therapy regimen component 110 may be configured to receive therapeutic feedback from the physician client computing platform 104. The therapeutic feedback may include modifications, acceptance, or denial of the effective therapy regimen as the current therapy regimen.

In some implementations, therapy regimen component 110 may be configured transmit the effective therapy regimen to the subject client computing platform 104 for presentation to the subject. In some implementations, therapy regimen component 110 may be configured to receive an acceptance of the effective therapy regimen as the current therapy regimen or a request for modification of the effective therapy regimen from subject client computing platform 104. In some implementations, the acceptance of the effective therapy regimen may be indicated by a lack of the request for modification.

Therapy regimen component 110 may be configured to define the effective therapy regimen as the current therapy regimen. In some implementations, defining the effective therapy regimen as the current therapy regimen may be based on the therapeutic feedback (i.e., modifications from the physician), the selected therapy regimen, the combination, the request for modification (from the subject), and/or other information. In some implementations, defining the effective therapy regimen as the current therapy regimen may be responsive to the acceptance included in the therapeutic feedback received and/or the acceptance received from the subject client computing platform 104.

Therapy regimen component 110 may be configured to transmit the current therapy regimen to the subject client computing platform 104 for presentation to the subject. The presentation of the current therapy regimen may be informative so that the subject is informed that the current therapy regimen has changed (to the effective therapy regimen). As such, the subject may be able to follow or attempted to follow the current therapy regimen to treat and/or improve their asthma symptoms. The current therapy regimen and/or other information transmitted may be conveyed by a graphical user interface via the subject client computing platform 104. The current therapy regimen conveyed by the graphical user interface may allow for incremental increases in asthma health and reduction in catastrophic medical incidents of the subject.

In some implementations, therapy regimen component 110 may be configured to generate notification information to present notifications. The notification information may be transmitted to the subject client computing platform 104 and/or to the physician client computing platform 104 to present the notifications. A notification for the physician may include the current therapy regimen or the effective therapy regimen, and/or other information related to the asthma of the subject. A notification for the subject may include the current therapy regimen or the effective therapy regimen, and/or other information related to the asthma of the subject. In some implementations, the notification information may include a pop-up window, a noise, haptics, and/or other notification information to present the notifications.

The transmission of the current therapy regimen, or in some implementations, the generation of the notification information may be responsive to defining a different one of the multiple therapy regimens as the current therapy regimen or adjusting the current therapy regimen. In some implementations, absence of the transmission of the current therapy regimen, or in some implementations, the generation of the notification information may indicate that the current therapy regimen that the subject is following does not require change to another therapy regimen or adjustments.

In some implementations, prospective therapy regimen component 112 may be configured to determine a prospective therapy regimen. The prospective therapy regimen may be appropriate for the one or more future physical locations at the future time for the future period of time based on the subject information, the condition impact assessments, the future location information, the environmental conditions based on the future location information, the current therapy regimen, and/or other information. In some implementations, based on the determined prospective therapy regimen, the current therapy regimen may be adjusted/newly determined and defined to proactively prevent the asthma prior to the future time at the future physical locations. Prospective therapy regimen component 112 may be configured to define the prospective therapy regimen as the current therapy regimen at the future time for the subject to follow or attempt to follow to treat their asthma.

In some implementations, prospective therapy regimen component 112 may be configured to determine the prospective therapy regimen for a future time based on machine learning of the subject information, the condition impact assessments, and/or other information. The machine learning may include known techniques. As such, the prospective therapy regimen may be inferred and defined as the current therapy regimen at the future time. In some implementations, the prospective therapy regimen may be adjusted as the subject information, the condition impact assessments, and/or other information updates.

In some implementations, the prospective therapy regimen may be determined a particular amount of time prior to the future time. For example, the prospective therapy regimen may be determined 5 days, 3 days, 2 days, or other amount of time prior to the future time to ensure that the prospective therapy regimen determined is based on the most current information to appropriately treat the asthma of the subject. In some implementations, the prospective therapy regimen may be defined as the current therapy regimen at a prior time prior to the future time. For example, the prior time may be 3 days or other prior time before the future time. The prior time or amount of time prior to the future time that the prospective therapy regimen is defined as the current therapy regimen may be defined by the physician, the subject, system 100, or other individuals.

Figures 3A, 3B:
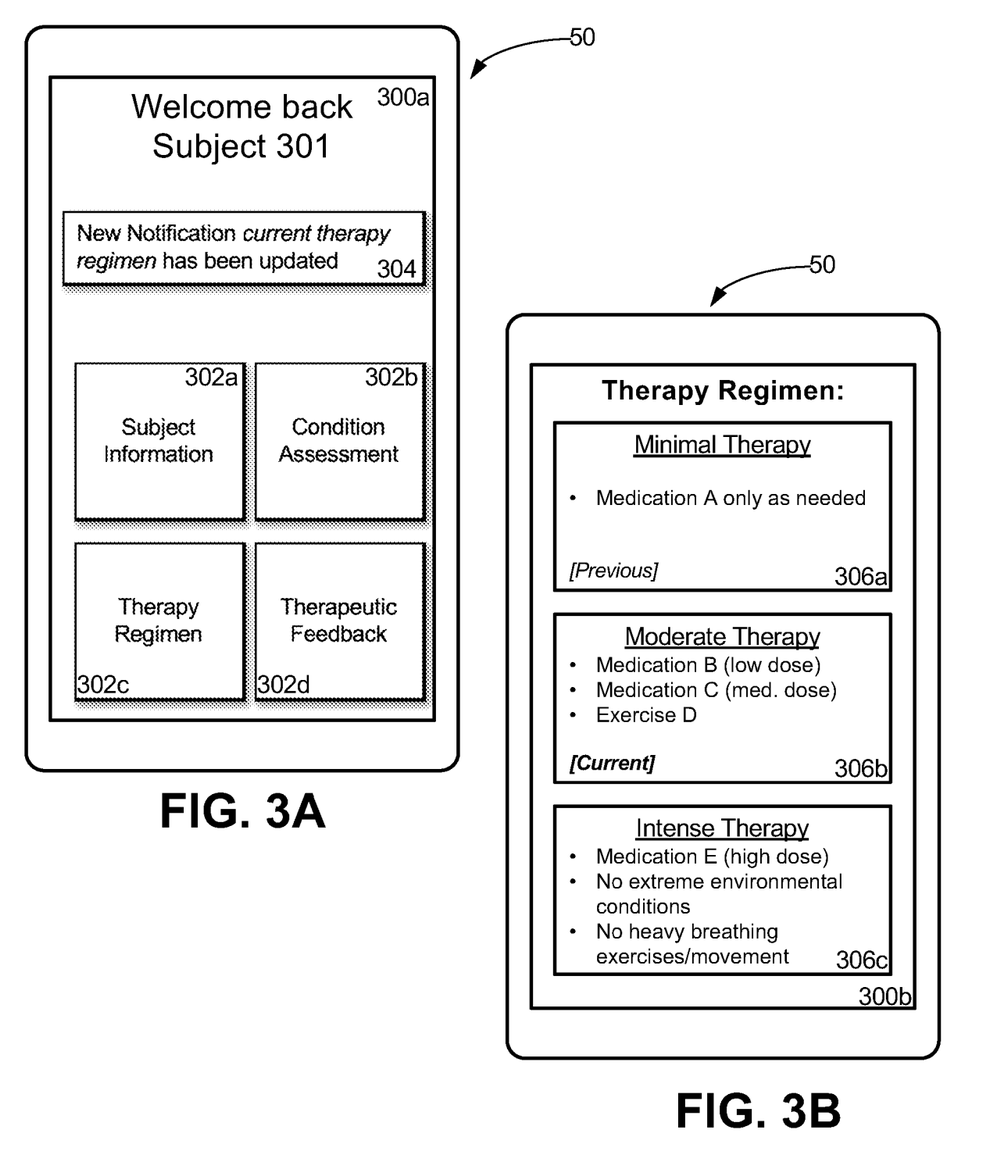
FIG. 3A-B illustrate example implementations of the system configured to determine a therapy regimen to treat asthma of a subject, in accordance with one or more implementations.

FIG. 3A-B illustrate example implementations, in accordance with one or more implementations. FIG. 3A illustrates a subject interface 300*a* on a smartphone 50 of a subject 301. Subject interface 300*a* may include virtual buttons 302*a*, 302*b*, 302*c*, and 302*d*. Virtual button 302*a-d* may be selected by subject 301 to present information related to their asthma. Virtual button 302*a* may represent subject information obtained (as described in FIG. 1) that may be presented upon selection of virtual button 302*a*. Virtual button 302*b* may represent a condition assessment (e.g., condition impact assessment as described in FIG. 1) of subject 301 that may be presented upon selection of virtual button 302*b*. Virtual button 302*c* may represent a specified and/or current therapy regimen (as described in FIG. 1) for subject 301 that may be presented upon selection of virtual button 302*c* and enable subject 301 to follow and treat their asthma. Virtual button 302*d* may represent therapeutic feedback (as described in FIG. 1) for subject 301 from the physician that may be presented upon selection of virtual button 302*d*. Notifications, such as notification 304, may be conveyed by subject interface 300*a*. Notification 304 may notify subject 301 that the current therapy regimen that they follow has been updated.

FIG. 3B illustrates subject interface 300*b* on smartphone 50, the same as smartphone 50 in FIG. 3A. Subject interface 300*b* may include a minimal therapy regimen 306*a*, a moderate therapy regimen 306*b*, and intense therapy regimen 306*c*. Subject interface 300*b* may convey that moderate therapy regimen 306*b* is the current therapy regimen that notification 304 referred to in FIG. 3A, changed from minimal therapy regimen 306*a*. Moderate therapy regimen 306*b* as the current therapy regimen may be based the subject information, the condition impact assessments, and/or other information as described in FIG. 1.

Referring back to FIG. 1, in some implementations, server(s) 102, client computing platform(s) 104, and/or external resources 124 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 124 may be operatively linked via some other communication media.

A given client computing platform 104 may include one or more processors configured to execute computer program components. The computer program components may be configured to enable an expert or subject associated with the given client computing platform 104 to interface with system 100 and/or external resources 124, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 124 may include sources of information outside of system 100, external entities participating with system 100, and/or other resources. In some implementations, some or all of the functionality attributed herein to external resources 124 may be provided by resources included in system 100.

Server(s) 102 may include electronic storage 126, one or more processors 128, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 126 may comprise non-transitory storage media that electronically stores information. The electronic storage media of electronic storage 126 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 126 may include one or more virtual storage resources (e.g., cloud storage, a virtual private network, and/or other virtual storage resources). Electronic storage 126 may store software algorithms, information determined by processor(s) 128, information received from server(s) 102, information received from client computing platform(s) 104, and/or other information that enables server(s) 102 to function as described herein.

Processor(s) 128 may be configured to provide information processing capabilities in server(s) 102. As such, processor(s) 128 may include one or more of a digital processor, an analog processor, a digital circuit designed to process information, an analog circuit designed to process information, a state machine, and/or other mechanisms for electronically processing information. Although processor(s) 128 is shown in FIG. 1 as a single entity, this is for illustrative purposes only. In some implementations, processor(s) 128 may include a plurality of processing units. These processing units may be physically located within the same device, or processor(s) 128 may represent processing functionality of a plurality of devices operating in coordination. Processor(s) 128 may be configured to execute components 108, 110, and/or 112, and/or other components. Processor(s) 128 may be configured to execute components 108, 110, and/or 112, and/or other components by software; hardware; firmware; some combination of software, hardware, and/or firmware; and/or other mechanisms for configuring processing capabilities on processor(s) 128. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, and/or 112 are illustrated in FIG. 1 as being implemented within a single processing unit, in implementations in which processor(s) 128 includes multiple processing units, one or more of components 108, 110, and/or 112 may be implemented remotely from the other components. The description of the functionality provided by the different components 108, 110, and/or 112 described below is for illustrative purposes, and is not intended to be limiting, as any of components 108, 110, and/or 112 may provide more or less functionality than is described. For example, one or more of components 108, 110, and/or 112 may be eliminated, and some or all of its functionality may be provided by other ones of components 108, 110, and/or 112. As another example, processor(s) 128 may be configured to execute one or more additional components that may perform some or all of the functionality attributed below to one of components 108, 110, and/or 112.

Figure 2:
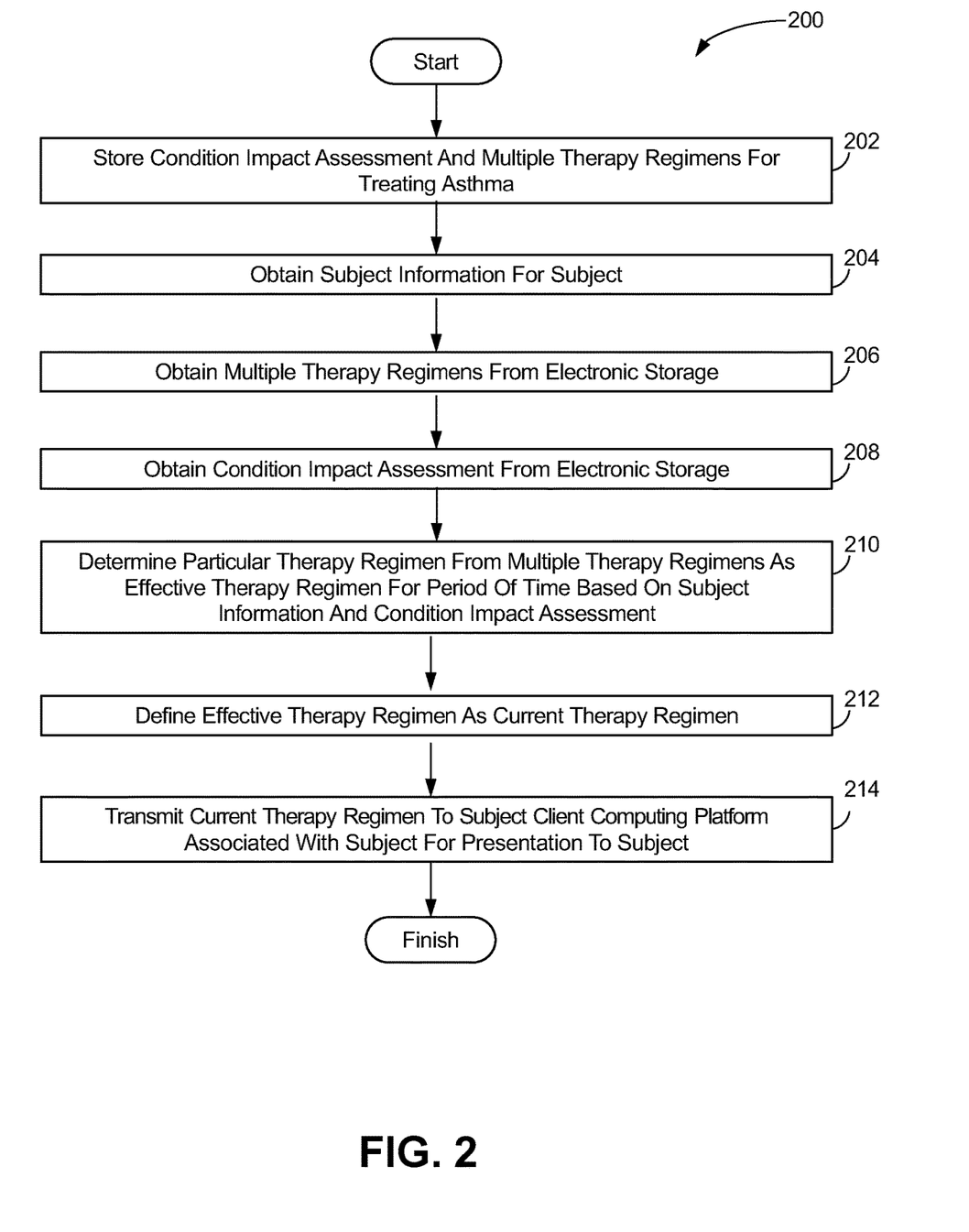
FIG. 2 illustrates a method to determine a therapy regimen to treat asthma of a subject, in accordance with one or more implementations.

FIG. 2 illustrates a method 200 to determine a therapy regimen to treat asthma of a subject, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include storing, in electronic storage, a condition impact assessment and multiple therapy regimens for treating asthma. The condition impact assessment may indicate a present impact of asthma on the subject. Individual therapy regimens may correspond to a particular impact of asthma on the subject and/or a particular condition of asthma. Operation 202 may be performed by electronic storage 126, in accordance with one or more implementations.

An operation 204 may include obtaining subject information for the subject. The subject information may include (i) environmental conditions at or around a physical location of the subject, (ii) results of remote diagnostic tests for the subject, and (iii) physician-certified condition information including results to physician-administered diagnostic tests for the subject. Operation 204 may be performed by one or more hardware processors configured by machine-readable instructions including a component that is the same as or similar to information obtainment component 108, in accordance with one or more implementations.

An operation 206 may include obtaining the multiple therapy regimens from the electronic storage. Operation 206 may be performed by one or more hardware processors configured by machine-readable instructions including a component that is the same as or similar to therapy regimen component 110, in accordance with one or more implementations.

An operation 208 may include obtaining the condition impact assessment from the electronic storage. Operation 208 may be performed by one or more hardware processors configured by machine-readable instructions including a component that is the same as or similar to therapy regimen component 110, in accordance with one or more implementations.

An operation 210 may include determining a particular therapy regimen from the multiple therapy regimens as an effective therapy regimen for a period of time based on the subject information and the condition impact assessment. Operation 210 may be performed by one or more hardware processors configured by machine-readable instructions including a component that is the same as or similar to therapy regimen component 110, in accordance with one or more implementations.

An operation 212 may include defining the effective therapy regimen as a current therapy regimen. Operation 212 may be performed by one or more hardware processors configured by machine-readable instructions including a component that is the same as or similar to therapy regimen component 110, in accordance with one or more implementations.

An operation 214 may include transmitting the current therapy regimen to a subject client computing platform associated with the subject for presentation to the subject. Operation 214 may be performed by one or more hardware processors configured by machine-readable instructions including a component that is the same as or similar to therapy regimen component 110, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to determine a therapy regimen to treat asthma of a subject, the system comprising:
    electronic storage configured to store a condition impact assessment and multiple therapy regimens for treating asthma, wherein the condition impact assessment indicates a present impact of asthma on the subject, wherein individual therapy regimens correspond to a particular impact of asthma on the subject and/or a particular condition of asthma;
    one or more processors configured by machine-readable instructions to:
        obtain subject information for the subject, wherein the subject information includes (i) environmental conditions at or around a physical location of the subject, (ii) results of remote diagnostic tests for the subject administered by the subject, and (iii) physician-certified condition information including results to physician-administered diagnostic tests for the subject;
        obtain the multiple therapy regimens from the electronic storage;
        obtain the condition impact assessment from the electronic storage;
        effectuate, via a subject client computing platform associated with the subject, presentation of the multiple therapy regimens;
        receive a selected therapy regimen of the multiple therapy regimens from the subject client computing platform;
        determine a particular therapy regimen from the multiple therapy regimens as an effective therapy regimen for a period of time based on the subject information, the condition impact assessment, and the selected therapy regimen;
        define the effective therapy regimen as a current therapy regimen; and
        effectuate, via the subject client computing platform, presentation of the current therapy regimen to the subject.

2. The system of claim 1, wherein determining the effective therapy regimen based on the subject information, the condition impact assessment, and the selected therapy regimen includes determining a combination of the selected therapy regimen and the particular therapy regimen.

3. The system of claim 1, wherein the one or more processors are further configured by the machine-readable instructions to:
    transmit the effective therapy regimen to a physician client computing platform associated with the physician for presentation to the physician; and
    receive therapeutic feedback from the physician client computing platform, wherein the therapeutic feedback includes modifications and/or acceptance of the effective therapy regimen as the current therapy regimen.

4. The system of claim 1, wherein the one or more processors are further configured by the machine-readable instructions to:
    transmit the effective therapy regimen to the subject client computing platform for presentation to the subject; and
    receive, from the subject client computing platform, an acceptance of the effective therapy regimen as the current therapy regimen or a request for modification of the effective therapy regimen.

5. The system of claim 1, wherein the one or more processors are further configured by the machine-readable instructions to:
    obtain future location information that indicates one or more future physical locations of the subject at a future time for a future period of time, wherein the environmental conditions are based on the future location information;
    determine a prospective therapy regimen for the one or more future physical locations at the future time for the future period of time based on the subject information; and
    define the prospective therapy regimen as the current therapy regimen at the future time.

6. The system of claim 5, wherein the future location information includes subject input obtained from the subject client computing platform.

7. The system of claim 1, wherein the one or more processors are further configured by the machine-readable instructions to:
    determine a prospective therapy regimen for a future time based on machine learning of the subject information.

8. The system of claim 1, wherein the period of time is a day, a set of days, or a week.

9. A method to determine a therapy regimen to treat asthma of a subject, the method comprising:
    storing, in electronic storage, a condition impact assessment and multiple therapy regimens for treating asthma, wherein the condition impact assessment indicates a present impact of asthma on the subject, wherein individual therapy regimens correspond to a particular impact of asthma on the subject and/or a particular condition of asthma;
    obtaining subject information for the subject, wherein the subject information includes (i) environmental conditions at or around a physical location of the subject, (ii) results of remote diagnostic tests for the subject administered by the subject, and (iii) physician-certified condition information including results to physician-administered diagnostic tests for the subject;
    obtaining the multiple therapy regimens from the electronic storage;
    obtaining the condition impact assessment from the electronic storage;
        effectuating, via a subject client computing platform associated with the subject, presentation of the multiple therapy regimens;
        receiving a selected therapy regimen of the multiple therapy regimens from the subject client computing platform;
    determining a particular therapy regimen from the multiple therapy regimens as an effective therapy regimen for a period of time based on the subject information, the condition impact assessment, and the selected therapy regimen;
    defining the effective therapy regimen as a current therapy regimen; and
    effectuating, via the subject client computing platform, presentation of the current therapy regimen to the subject.

10. The method of claim 9, wherein determining the effective therapy regimen based on the subject information, the condition impact assessment, and the selected therapy regimen includes determining a combination of the selected therapy regimen and the particular therapy regimen.

11. The method of claim 9, further comprising:
    transmitting the effective therapy regimen to a physician client computing platform associated with the physician for presentation to the physician; and
    receiving therapeutic feedback from the physician client computing platform, wherein the therapeutic feedback includes modifications and/or acceptance of the effective therapy regimen as the current therapy regimen.

12. The method of claim 9, further comprising:
    transmitting the effective therapy regimen to the subject client computing platform for presentation to the subject; and
    receiving, from the subject client computing platform, an acceptance of the effective therapy regimen as the current therapy regimen or a request for modification of the effective therapy regimen.

13. The method of claim 9, further comprising:
    obtaining future location information that indicates one or more future physical locations of the subject at a future time for a future period of time, wherein the environmental conditions are based on the future location information;
    determining a prospective therapy regimen for the one or more future physical locations at the future time for the future period of time based on the subject information; and
    defining the prospective therapy regimen as the current therapy regimen at the future time.

14. The method of claim 13, wherein the future location information includes subject input obtained from the subject client computing platform.

15. The method of claim 9, further comprising:
    determining a prospective therapy regimen for a future time based on machine learning of the subject information.

16. The method of claim 9, wherein the period of time is a day, a set of days, or a week.

* * * * *